United States Patent
Ko

(10) Patent No.: US 12,419,926 B2
(45) Date of Patent: Sep. 23, 2025

(54) **COMPOSITION FOR PREVENTING OR TREATING CANCER COMPRISING *ANGELICA GIGAS, ACONITUM CARMICHAELI* DEBEAUX, AND *ZINGIBER OFFICINALE* ROSCOE MIXED EXTRACT AS ACTIVE INGREDIENT**

(71) Applicant: UNIVERSITY-INDUSTRY COOPERATION GROUP OF KYUNG HEE UNIVERSITY, Gyeonggi-do (KR)

(72) Inventor: Seong-Gyu Ko, Seoul (KR)

(73) Assignee: UNIVERSITY-INDUSTRY COOPERATION GROUP OF KYUNG HEE UNIVERSITY, Gyeonggi-do (KR)

( * ) Notice: Subject to any disclaimer, the term of this patent is extended or adjusted under 35 U.S.C. 154(b) by 654 days.

(21) Appl. No.: 17/639,040

(22) PCT Filed: Aug. 28, 2020

(86) PCT No.: PCT/KR2020/011530
§ 371 (c)(1),
(2) Date: Feb. 28, 2022

(87) PCT Pub. No.: WO2021/040449
PCT Pub. Date: Mar. 4, 2021

(65) Prior Publication Data
US 2022/0323526 A1    Oct. 13, 2022

(30) Foreign Application Priority Data
Aug. 28, 2019    (KR) ........................ 10-2019-0106051

(51) Int. Cl.
| | | |
|---|---|---|
| *A61K 36/00* | (2006.01) | |
| *A61K 36/232* | (2006.01) | |
| *A61K 36/714* | (2006.01) | |
| *A61K 36/9068* | (2006.01) | |
| *A61P 11/00* | (2006.01) | |
| *A61P 35/00* | (2006.01) | |

(52) U.S. Cl.
CPC .......... *A61K 36/232* (2013.01); *A61K 36/714* (2013.01); *A61K 36/9068* (2013.01); *A61P 11/00* (2018.01); *A61P 35/00* (2018.01); *A61K 2236/331* (2013.01); *A61K 2236/333* (2013.01)

(58) Field of Classification Search
None
See application file for complete search history.

(56) References Cited

U.S. PATENT DOCUMENTS

2016/0243180 A1    8/2016    Ko et al.

FOREIGN PATENT DOCUMENTS

| CN | 104644631 A | 5/2015 |
|---|---|---|
| CN | 106344518 A | 1/2017 |
| CN | 109260443 A | 1/2019 |
| CN | 110124004 A | 8/2019 |
| JP | 2006117663 A | 5/2006 |
| KR | 10-2005-0047207 A | 5/2005 |
| KR | 10-2016-0084175 A | 7/2016 |
| KR | 10-2017-0045088 A | 5/2017 |
| WO | 2008139952 A1 | 11/2008 |

OTHER PUBLICATIONS

Abdullah et al. (2010) African Journal of Biochemistry Research, vol. 4 (4): pp. 134-142. (Year: 2010).*
Lee et al. (2009) The American Journal of Chinese Medicine vol. 37, No. 1., 127-142. (Year: 2009).*
Li et al. (2018) Chem. Biodiversity 15: e1800147 (8 pages). (Year: 2018).*
Lima et al. (2018) Phytotherapy Research 32: 1885-1907. (Year: 2018).*
Pereira et al. (2011) Journal of BUON 16: 414-424. (Year: 2011).*
Ramakrishnan (2013) IJMPS vol. 3, Issue 5, 11-20. (Year: 2013).*
Ren et al. (2017) Molecules 22, 267 (14 pages) (Year: 2017).*
Liang, Ying et al. "Anti-cancer and anti-inflammatory new vakognavine-type alkaloid from the roots of Aconitum carmichaelii" Tetrahedron Letters 57 (2016) 5881-5884.

(Continued)

*Primary Examiner* — Russell G Fiebig
(74) *Attorney, Agent, or Firm* — Edwin S. Flores; Daniel J. Chalker; Chalker Flores, LLP

(57) ABSTRACT

The present invention relates to a composition for preventing or treating cancer comprising a mixed extract of *Angelica gigas, Aconitum carmichaeli* Debeaux, and *Zingiber officinale* Roscoe as an active ingredient, more particularly to a pharmaceutical composition, a food composition, and a feed composition for preventing or treating cancer including a mixed extract of *Angelica gigas, Aconitum carmichaeli* Debeaux, and *Zingiber officinale* Roscoe as an active ingredient; a method for preventing or treating cancer comprising a step of administering the pharmaceutical composition; and a use for preventing or treating cancer.

*Angelica gigas, Aconitum carmichaeli* Debeaux, or *Zingiber officinale* Roscoe of the present invention exhibits excellent cancer treatment effects, and therefore can be included in a pharmaceutical composition or a food as an active ingredient to be used in development of cancer treatment or amelioration agents and the like.

4 Claims, 18 Drawing Sheets

(56) References Cited

OTHER PUBLICATIONS

Prasad, Sahdeo et al., "Ginger and its Constituents: Role in Prevention and Treatment of Gastrointestinal Cancer", Gastroenterology Research and Practice, 2015, vol. 2015, p. 1-11.
Tang, Su-Ni et al., "Chemopreventive Effects of Korean Angelica versus its Major Pyranocoumarins on Two Lineages of Transgenic Adenocarcinoma of Mouse Prostate Carcinogenesis", Cancer Prevention Research, 20150901, vol. 8, No. 9, p. 835-844, DOI: 10.1158/1940-6207.CAPR-15-0051.
Lee, Hyo Jeong et al. "In vivo Anti-Cancer Activity of Korean Angelica Gigas and its Major Pyranocoumarin Decursin" The American Journal of Chinese Medicine, 2009, vol. 37, No. 1, 127-142.
Extended European Search Report, EP 20856687.7 dated Apr. 11, 2023.

* cited by examiner

GASTRIC CANCER

AGS

JI017 (hr)   0   8   16   24

Cleaved Casp9

Cleaved Casp3

β-actin

OVARIAN CANCER

A2780

JI017 (hr)   0   8   16   24

Cleaved Casp9

Cleaved Casp3

β-actin

COLORECTAL CANCER

HCT-116

JI017 (hr)    0    8    16    24

Cleaved Casp9

Cleaved Casp3

β-actin

BREAST CANCER

MCF-7

JI017 (hr)    0    8    16    24

Cleaved Casp9

Cleaved Casp3

β-actin

COMPOSITION FOR PREVENTING OR TREATING CANCER COMPRISING ANGELICA GIGAS, ACONITUM CARMICHAELI DEBEAUX, AND ZINGIBER OFFICINALE ROSCOE MIXED EXTRACT AS ACTIVE INGREDIENT

CROSS-REFERENCE TO RELATED APPLICATIONS

This application is the National Stage of International Application No. PCT/KR2020/011530, filed on Aug. 28, 2020, claiming the priority of KR 10-2019-0106051, filed on Aug. 28, 2019, the content of each of which is incorporated by reference herein.

TECHNICAL FIELD

The present invention relates to a composition for preventing or treating cancer including a mixed extract of *Angelica gigas, Aconitum carmichaeli* Debeaux, and *Zingiber officinale* Roscoe as an active ingredient, and more particularly to a pharmaceutical composition, a food composition, and a feed composition for preventing or treating cancer including a mixed extract of *Angelica gigas, Aconitum carmichaeli* Debeaux, and *Zingiber officinale* Roscoe as an active ingredient; a method for preventing or treating cancer including a step of administering the pharmaceutical composition; and a use for preventing or treating cancer.

BACKGROUND ART

Cancer has been the leading cause of disease death in Korea, and more than about 100,000 people are diagnosed with cancer, and more than about 60,000 people died of cancer every year. Cancer, as the leading cause of death in the world as well, is one of the incurable diseases that humanity needs to solve. Accordingly, huge capital investment has been made and intensive research has been conducted to develop therapeutic agents for cancer worldwide. Since smoking, UV rays, chemicals, foods, and other environmental factors are known as carcinogens causing cancer, it is difficult to prevent or treat cancer due to the various factors as described above, and cancer occurs in various locations of the body. Also, different types of therapeutic agents are used according to types of cancer occurring in different locations of the body.

Substances currently used as therapeutic agents are considerably toxic and cannot selectively remove target cancer cells. Such therapeutic agents are not effective, and side effects may be caused thereby. Therefore, there is a need to develop an anticancer drug less toxic and more effective in preventing and treating cancer.

Meanwhile, *Angelica gigas* is a perennial plant belonging to the family Apiaceae, and dried roots of *Angelica gigas* are sweet and hot and have a warming medicinal property. *Angelica gigas* has effects on enriching the blood when there is poverty of the blood, increasing blood flow in coronary arteries, and promoting erythropoiesis.

*Aconitum carmichaeli* Debeaux is prepared by processing lateral roots of aconite belonging to the family Ranunculaceae. In general, salted aconite is desalted by soaking in water and changing water twice to three times every day. When the aconite is completely desalted, the aconite is boiled together with licorice and black beans until the inside is cooked through. When the tongue is not numb with a cut piece of the boiled aconite, the aconite is peeled, cut into thin slices or two or three pieces, and dried in the sun. A product obtained therefrom is referred to as *Aconitum carmichaeli* Debeaux, which has a spicy and hot taste, opens a gateway to the human body, strengthens the base of the human body, and has effects on warming the spleen and stomach.

*Zingiber officinale* Roscoe is prepared by using dried rhizomes of ginger and has a particular smell and spicy and hot medicinal properties. The outer bark is grayish-yellow, and the outer surface is grayish-white with white powder attached thereto. *Zingiber officinale* Roscoe is effective on ameliorating symptoms such as cold and mild pain in the chest and stomach, abdominal coldness, dyspepsia, vomiting, and diarrhea. Also, *Zingiber officinale* Roscoe is used to treat weak pulse, cold and tingling limbs, chronic cough caused by cold air, shortness of breath, coldness in the lower abdomen, and dysenteric diarrhea. Pharmacological effects include promoting gastric secretion, activating peristalsis of intestinal tract, accelerating digestion, reducing vomiting, and stimulating the heart to increase blood pressure and promote blood circulation. Anti-inflammatory, analgesic, and antibacterial actions are also obtained thereby.

As described above, although various pharmacological effects of *Angelica gigas, Aconitum carmichaeli* Debeaux, and *Zingiber officinale* Roscoe are known, anticancer effects of a mixed extract thereof have not been discovered so far, and no research thereon has been conducted.

Technical Problem

With this background, as a result of intensive efforts to develop a novel anticancer drug, the present inventors have found that a mixed extract of *Angelica gigas, Aconitum carmichaeli* Debeaux, and *Zingiber officinale* Roscoe has effects on specifically suppressing proliferation of various cancer cells and reducing cancer cell viability, thereby completing the present invention.

Technical Solution

An object of the present invention is to provide a pharmaceutical composition for preventing or treating cancer including a mixed extract of *Angelica gigas, Aconitum carmichaeli* Debeaux, and *Zingiber officinale* Roscoe as an active ingredient.

Another object of the present invention is to provide a food composition for preventing or alleviating cancer including a mixed extract of *Angelica gigas, Aconitum carmichaeli* Debeaux, and *Zingiber officinale* Roscoe as an active ingredient.

Another object of the present invention is to provide a feed composition for preventing or alleviating cancer including a mixed extract of *Angelica gigas, Aconitum carmichaeli* Debeaux, and *Zingiber officinale* Roscoe as an active ingredient.

Another object of the present invention is to provide a method for preventing or treating cancer including administering the pharmaceutical composition to an individual.

Advantageous Effects

Since the mixed extract of *Angelica gigas, Aconitum carmichaeli* Debeaux, and *Zingiber officinale* Roscoe according to the present invention has excellent therapeutic effects on cancer, the mixed extract may be included in pharmaceutical compositions or foods as an active ingredient to be used for development of therapeutic or alleviating agents of cancer.

Debeaux, and *Zingiber officinale* Roscoe with a mixing ratio of 2:1:1 in colorectal cancer cells evaluated by Western blot analysis.

Figure 28:
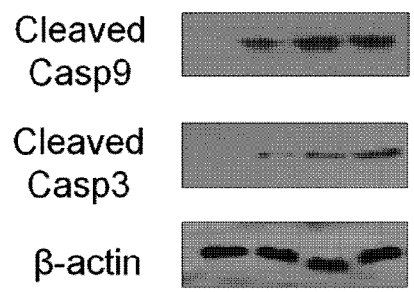

FIG. 28 is photographs showing an anticancer mechanism of a mixed extract of *Angelica gigas, Aconitum carmichaeli* Debeaux, and *Zingiber officinale* Roscoe with a mixing ratio of 2:1:1 in breast cancer cells evaluated by Western blot analysis.

BEST MODE

An aspect of the present invention to achieve the above-described objects provides a pharmaceutical composition for preventing or treating cancer including a mixed extract of *Angelica gigas, Aconitum carmichaeli* Debeaux, and *Zingiber officinale* Roscoe as an active ingredient.

As used herein, the term *"Angelica gigas"* has a branched root with a conical or narrow long conical shape usually 15 cm to 25 cm in length and 2 cm to 5 cm in diameter. The external surface is pale yellowish brown to blackish brown with irregular longitudinal wrinkles and spot-shaped remains of fibrous roots. The crown is broad, usually with remains of stems and leaves, and the xylem is white or yellowish white. *Angelica gigas* is known to nourish and enrich the blood due to effects on tonifying blood and activating blood circulation, effects on regulating menstruation to alleviate pain, and effects on loosening the bowel to relieve constipation.

As used herein, the term *"Aconitum carmichaeli* Debeaux" refers to a product obtained by heat-treating lateral roots of *Aconitum carmichaeli* Debeaux, also known as aconite root, belonging to the family Ranunculaceae. Since raw aconite is poisonous, it is common to use aconite after processing. *Aconitum carmichaeli* Debeaux is known to raise energy to restore stamina.

As used herein, the term *"Zingiber officinale* Roscoe" is a product obtained by drying rhizomes of ginger that is a perennial herbaceous plant belonging to the family Zingiberaceae under the sun or heat-treating them over low heat. *Zingiber officinale* Roscoe is known to have a hotter property than ginger and effects on warming the stomach and intestines.

As used herein, the term "extract" refers to a substance obtained from a certain substance by extraction, and specifically encompasses the extract itself and all possible formulations of the extract, such as a liquid extract obtained by extraction according to the present invention, a diluent or concentrate of the liquid extract, a dehydrated product obtained by drying the liquid extract, a crude purified product or purified product of the liquid extract, or any mixture thereof.

Methods of preparing the extract are not particularly limited and may be any method well known in the art. Non-limiting examples of the extraction method may include solvent extraction, ultrasonic extraction, filtration, and reflux extraction which may be used alone or in a combination of at least two thereof.

In the present invention, types of a solvent used to obtain the extract are not particularly limited, and any solvent well known in the art may be used. Non-limiting examples of the solvent may include water, a $C_1$-$C_4$ alcohol, or any mixed solvent thereof which may be used alone or in a combination of at least two thereof. Specifically, the solvent may be ethanol.

As used herein, the "mixed extract" may be prepared by mixing *Angelica gigas, Aconitum carmichaeli* Debeaux, and *Zingiber officinale* Roscoe and then obtaining an extract therefrom or by obtaining *Angelica gigas* extract, *Aconitum carmichaeli* Debeaux extract, and *Zingiber officinale* Roscoe extract and then mixing the extracts.

As used herein, the term "cancer" refers to a tumor abnormally grown due to autonomous overgrowth of body tissues or a disease forming tumors.

Specifically, the cancer may be lung cancer (e.g., non-small cell lung cancer, small cell lung cancer, or malignant mesothelioma), mesothelioma, pancreatic cancer (e.g., pancreatic duct cancer or pancreatic endocrine tumor), pharyngeal cancer, laryngeal cancer, esophageal cancer, gastric cancer (e.g., papillary adenocarcinoma, mucinous adenocarcinoma, or adenosquamous carcinoma), duodenal cancer, small intestine cancer, colorectal cancer (e.g. colon cancer, rectal cancer, anal cancer, familial colorectal cancer, hereditary nonpolyposis colorectal cancer, or gastrointestinal stromal tumor), breast cancer (e.g., invasive ductal cancer, non-invasive ductal cancer, or inflammatory breast cancer), ovarian cancer (e.g., epithelial ovarian carcinoma, extratesticular germ cell tumor, ovarian germ cell tumor, or ovarian low grade serious tumor), testis cancer, prostate cancer (e.g., hormone-dependent prostate cancer or hormone-independent prostate cancer), liver cancer (e.g., hepatocellular carcinoma, primary liver cancer, or extrahepatic bile duct cancer), thyroid cancer (e.g., medullary thyroid carcinoma), kidney cancer (e.g., renal cell carcinoma or transitional cell carcinoma of the renal pelvis and ureter), uterine cancer (e.g., cervical cancer, cancer of uterine body, or uterine sarcoma), brain tumors (e.g., medulloblastoma, glioma, pineal astrocytoma, pilocytic astrocytoma, diffuse astrocytoma, anaplastic astrocytoma, or pituitary adenoma), retinoblastoma, skin cancer (e.g., basal cell carcinoma or malignant melanoma), sarcoma (e.g., rhabdomyosarcoma, leiomyosarcoma, or soft tissue sarcoma), malignant bone tumor, bladder cancer, blood cancer (e.g., multiple myeloma, leukemia, malignant lymphoma, Hodgkin's disease, or chronic myeloproliferative disease), or cancer of unknown primary. More specifically, the cancer may be gastric cancer, ovarian cancer, prostate cancer, liver cancer, breast cancer, lung cancer, and colorectal cancer, without being limited thereto.

As used herein, the term "prevention" refers to all activities that inhibit or delay the growth of cancer cells by administering the pharmaceutical composition according to the present invention.

As used herein, the term "treatment" refers to all activities that alleviate or beneficially change symptoms of a subject having or suspected to have a cancer by administering the pharmaceutical composition.

In the present invention, the composition is preferably administered to humans but may also be administered to livestock, such as cattle, horses, sheep, pigs, goats, camels, antelopes, dogs, or cats, which have an inflammatory disease or cancer, and there is a possibility of suppressing or alleviating cancer by administering the composition of the present invention.

The content of mixed extract of *Angelica gigas, Aconitum carmichaeli* Debeaux, and *Zingiber officinale* Roscoe contained in the pharmaceutical composition of the present invention may be in the range of 0.0001 wt % to 80 wt %, 0.0001 wt % to 50 wt %, more specifically 0.01 wt % to 20 wt % based on a total weight of a final composition, but is not limited to.

Specifically, the pharmaceutical composition of the present invention may further include a pharmaceutically acceptable carrier, excipient, or diluent, and the carrier may further include a carrier which does not occur naturally.

More specifically, the carrier, excipient, and diluent that may be contained in the pharmaceutical composition may be lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, polycaprolactone, poly lactic acid, poly-L-lactic acid, and mineral oil.

The pharmaceutical composition may be formulated in the form of an oral administration such as powders, granules, tablets, capsules, suspensions, emulsions, syrups, and aerosols, external applications, suppositories, and sterile injection solutions according to methods commonly used in the art. The carrier may have various amorphous shaped carriers, microspheres, nanofibers, and the like.

For formulations, a diluent or excipient such as a filler, an extender, a binder, a humectant, a disintegrant, and a surfactant which are commonly available in the art may be used.

Solid preparations for oral administration include tablets, pills, powders, granules, capsules, and the like, and such a solid preparation is formulated by mixing one or more excipients, such as starch, calcium carbonate, sucrose, lactose, and gelatin with the extract or fractions thereof. Also, in addition to a simple excipient, a lubricant such as magnesium stearate and talc may also be used.

Liquid preparations for oral administration may be suspensions, formulations for internal use, emulsions, syrups, or the like and may include various excipients such as a humectant, a sweetener, a flavor, and a preservative in addition to a simple diluent such as water and liquid paraffin.

Formulations for parental administration may include sterile aqueous solutions, non-aqueous solvents, suspensions, emulsions, lyophilizates, suppositories, and the like. The non-liquid solvents and suspensions may be propylene glycol, polyethylene glycol, vegetable oils such as olive oil, injectable esters such as ethyl oleate.

Another aspect of the present invention to achieve the above-described objects provides a food composition for preventing or alleviating cancer including a mixed extract of *Angelica gigas, Aconitum carmichaeli* Debeaux, and *Zingiber officinale* Roscoe as an active ingredient.

In this regard, the terms *"Angelica gigas", "Aconitum carmichaeli* Debeaux", *"Zingiber officinale* Roscoe", "extract", "cancer", and "prevention" are as described above.

As used herein, the term "alleviation" refers to all actions that decrease parameters, e.g., the degree of symptoms, related to a condition to be treated by administering the composition.

Since the mixed extract of *Angelica gigas, Aconitum carmichaeli* Debeaux, and *Zingiber officinale* Roscoe according to the present invention exhibits excellent anticancer effects, the mixed extract may be contained in a food composition for preventing or alleviating cancer. Since the food composition may be ingested routinely, high effects on preventing or alleviating cancer may be expected.

As used herein, the term "food" may include all foods that are considered within conventional meaning such as meat, sausages, bread, chocolate, candies, snacks, confectionery, pizza, ramen, other noodles, gum, dairy products including ice cream, various soups, beverages, tea, drinks, alcoholic beverages, multivitamin complexes, and health functional food, but is not particularly limited as long as the food includes *Angelica gigas, Aconitum carmichaeli* Debeaux, and *Zingiber officinale* Roscoe of the present invention.

As used herein, the term "health functional food" means food manufactured and processed with functional raw materials or ingredients beneficial to human health under Health Functional Food Act No. 6727, and the term "functional" means controlling nutrients for the structure or functions of the human body or providing beneficial effects to health purposes, such as physiological effects. Meanwhile, health food refers to a food having an effect on maintaining or promoting health conditions compared to general foods, and health supplement food refers to a food for health supplement. In some cases, the terms "health functional food", "health food", and "health supplement food" may be used interchangeably.

The *Angelica gigas, Aconitum carmichaeli* Debeaux, and *Zingiber officinale* Roscoe of the present invention may be added as-is or may be used together with other foods or other food ingredients and may be appropriately used according to any method commonly used in the art.

The food of the present invention may be prepared by way of a method commonly used in the art, and raw materials and ingredients typically used in the art may be added thereto for the preparation thereof. Specifically, the food composition may further include a physiologically acceptable carrier, but types of the carrier are not particularly limited, and any carrier commonly used in the art may be used. In addition, the food composition may include food additives such as a preservative, a disinfectant, an antioxidant, a coloring agent, a color-developing agent, a bleaching agent, a seasoning, a sweetener, a flavor, a swelling agent, a fortifier, an emulsifier, a thickener, a film-forming agent, a gum base agent, an antifoaming agent, a solvent, and an enhancer. The additives may be selected according to the type of food and used in an appropriate amount.

In addition, the food may be prepared into any formulation regarded as a food without limitation. The food composition of the present invention may be prepared into various formulations. Unlike general drugs, the food composition including a food as an ingredient is free from side effects that may occur upon long-term intake of a drug and has high portability, and therefore the food composition of the present invention may be ingested as an aid for preventing or alleviating cancer.

The mixed extract of *Angelica gigas, Aconitum carmichaeli* Debeaux, and *Zingiber officinale* Roscoe of the present invention may be added to a food composition in various amounts (wt %) as long as preventive or alleviating effects on cancer are obtained. Specifically, the mixed extract may be contained in a food composition in an amount of 0.00001 wt % to 100 wt % or 0.01 wt % to 80 wt % based on a total weight of the food composition without being limited thereto. However, when prolonged intake is intended for the purpose of health and hygiene, the effective doses may be below the above range. In addition, since there is no safety problem, the active ingredient may be used in an amount above the range.

Another aspect of the present invention to achieve the above-described objects provides a feed composition for preventing or alleviating cancer including a mixed extract of *Angelica gigas, Aconitum carmichaeli* Debeaux, and *Zingiber officinale* Roscoe as an active ingredient.

In this regard, the terms *"Angelica gigas", "Aconitum carmichaeli* Debeaux", *"Zingiber officinale* Roscoe", "extract", "cancer", "prevention", and "alleviation" are as described above.

Since the mixed extract of *Angelica gigas, Aconitum carmichaeli* Debeaux, and *Zingiber officinale* Roscoe according to the present invention has excellent therapeutic effects on cancer, the mixed extract may be contained in a feed composition for the purpose of prevention or alleviation of cancer. In addition, since the feed composition may be ingested routinely, high effects on preventing or alleviating cancer may be expected.

As used herein, the term "feed" refers to any natural or artificial diet, a meal, or components thereof for animals to eat, ingest, and digest.

Types of the feed are not particularly limited, and any feed commonly used in the art may be used. Non-limiting examples of the feeds include: vegetable feeds such as grains, roots/fruits, food processing by-products, algae, fibers, pharmaceutical by-products, oils and fats, starches, gourds, or grain by-products; and animal feeds such as proteins, inorganic materials, oils and fats, minerals, single-cell proteins, animal planktons, or foods. These feeds may be used alone or in a combination of at least two thereof.

Another aspect of the present invention to achieve the above-described objects provides a method for preventing or treating cancer including administering the pharmaceutical composition to an individual.

In this regard, the "pharmaceutical composition", "cancer", "prevention", and "treatment" are as described above.

Since the pharmaceutical composition of the present invention has preventive or therapeutic effects on cancer, the method including the step of administering the composition to an individual according to the present invention may be effectively used to prevent or treat cancer.

As used herein, the term "administration" refers to introduction of the composition of the present invention into an individual by way of an appropriate method.

As used herein, the term "administration" refers to introduction of the composition of the present invention into a patient by way of an appropriate method, and an administration route of the composition may be any conventional route that enables delivery of the composition to target tissue, for example, intraperitoneal administration, intravenous administration, intramuscular administration, subcutaneous administration, intradermal administration, oral administration, topical administration, or intranasal administration, without being limited thereto.

As used herein, the term "individual" refers to all animals including humans with cancer or at risk of developing cancer such as mice, rats, and livestock. Specific examples thereof may be mammals including humans, without being limited thereto.

Another aspect of the present invention to achieve the above-described objects provides a use of a mixed extract of *Angelica gigas*, *Aconitum carmichaeli* Debeaux, and *Zingiber officinale* Roscoe as an active ingredient for preventing or treating cancer.

In this regard, the terms *"Angelica gigas"*, *"Aconitum carmichaeli* Debeaux*"*, *"Zingiber officinale* Roscoe*"*, "extract", "cancer", "prevention", and "treatment" are as described above.

MODE FOR INVENTION

Hereinafter, the present invention will be described in more detail with reference to the following examples. However, the following examples are merely presented to exemplify the present invention, and the scope of the present invention is not limited thereto.

Example 1: Preparation of Mixed Extract of *Angelica gigas*, *Aconitum carmichaeli* Debeaux, and *Zingiber officinale* Roscoe

*Angelica gigas*, *Aconitum carmichaeli* Debeaux, and *Zingiber officinale* Roscoe were mixed in weight ratios of (1) 2:1:1, (2) 4:1:1, and (3) 2:3:1 (w/w) and the mixtures were added to an extractor. 8 to 10 times of 70% ethanol was added thereto, followed by extraction for 2 to 3 hours. The extract was filtered, and a filtrate was concentrated under reduced pressure and dried to obtain mixed extracts of *Angelica gigas*, *Aconitum carmichaeli* Debeaux, and *Zingiber officinale* Roscoe.

Example 2: Culture of Cancer Cells

Cancer cells purchased from American Type Culture Collection (ATCC) were used in experiments of the present invention. In addition, the cells were incubated in an incubator using an RPMI 1640 medium supplemented with 10% heat-inactivated fetal bovine serum (FBS) and a 100 U/mL antibiotic-antifungal agent (Invitrogen) at 37° C. under 5% $CO_2$ conditions.

Example 3: Identification of Cancer Cell Viability by MTT Assay

Cell viability was measured by an MTT assay to identify effects of the mixed extract of the present invention on suppressing the growth of cancer cells and a role thereof as an anticancer drug.

Specifically, gastric cancer, ovarian cancer, prostate cancer, liver cancer, breast cancer, lung cancer, and colorectal cancer cells were used, and more specifically, cancer cells (AGS and MKN45 for gastric cancer, A2780, OVCAR3, and LNCAP for ovarian cancer, PC3 and DU145 for prostate cancer, K-Hep-1 and HepG2 for liver cancer, SKBR3 and MCF7 for breast cancer, H1299 and H460 for lung cancer, and HCT116 and LOVO cells for colorectal cancer) were inoculated onto a 96-well plate at a density of $3\times10^3$ cells/well and cultured for 24 hours. Subsequently, the cells were treated with 100 μg/mL of each of four types of the mixed extracts according to the present invention and further cultured for 24 hours. After culturing, an MTT solution (0.5 mg/mL) was added to the wells and maintained in a dark room at 37° C. for 2 hours. After removing the culture medium, absorbance was identified with formazan dissolved in DMSO and an ELISA reader at 570 nm.

As a result, as shown in FIGS. 1 to 7, it was confirmed that growth rates of cancer cells was reduced in all cancer cells when treated with the mixed extract, and the growth rate was the lowest at the mixing ratio of (1) 2:1:1.

Based thereon, it was confirmed that the mixed extract of the present invention suppressed the growth of cancer cells, and efficacy was the highest at the mixing ratio of (1) 2:1:1.

Example 4: Colony Formation Assay

In order to identify the ability of the mixed extract of *Angelica gigas*, *Aconitum carmichaeli* Debeaux, and *Zingiber officinale* Roscoe of the present invention to suppress cancer cell growth and colony formation, gastric cancer, ovarian cancer, prostate cancer, liver cancer, breast cancer, lung cancer, and colorectal cancer cells were treated with the mixed extract, and colony formation and growth rates of the cancer cells were evaluated.

More specifically, AGS cells were used as the gastric cancer, A2780 and OVCAR3 cells were used as the ovarian cancer, DU145 and PC3 cells were used as the prostate cancer, HEPG2 and SKHEP1 cells were used as the liver cancer, MCF7 and SKBR3 cells were used as the breast cancer, A549, H1299, and H460 cells were used as the lung cancer, and HCT116 and LOVO cells were used for the colorectal cancer. Cancer cells were inoculated onto a 6-well plate at a density of 3×10³ cells/well and cultured for 24 hours, and then the cells were treated with the mixed extracts of the present invention with mixing ratios of (1) 2:1:1, (2) 4:1:1, and (3) 2:3:1 as described above and further cultured for 24 hours. Then, the cells were cultured for 10 days for colony formation. Formation of colonies was confirmed by staining the colonies with 50% methanol in which 0.1% crystal violet (Amersco, Solon, OH, USA) was dissolved and 10% glacial acetic acid.

As a result, as shown in FIGS. 8 to 14, it was visually confirmed that the size of the stained cells decreased by treating the cancer cells with the mixed extracts compared with a negative control based on the degrees of staining. It was confirmed that the abilities to suppress colony formation vary in accordance with the mixing ratio, and the highest ability to suppress formation of colonies was obtained at the mixing ratio of (1) 2:1:1.

As a result, it was confirmed that the mixed extract suppressed formation of cancer cell colonies, and thus the mixing ratio of (1) 2:1:1 was selected based thereon and used in subsequent experiments.

Example 5: Identification of Ability of Mixed Extract to Suppress Growth of Cancer Cell Colony by MTT Assay In order to identify the ability of the mixed extract of the present invention to suppress cancer cell growth and colony formation, gastric cancer, ovarian cancer, prostate cancer, liver cancer, breast cancer, lung cancer, and colorectal cancer cells were treated with the mixed extract and formation of colonies, and growth rates were identified.

Specifically, the cells were treated with the mixed extract having a mixed ratio of 2:1:1 selected in Example 4. A test method of the MTT assay is as described above in Example 3.

As a result, as shown in FIGS. 15 to 21, it was confirmed that the growth rate of the cancer cell colonies decreased by treatment with the mixed extract compared to a negative control, and the cancer cell growth also decreased in most cases as a concentration increased.

Therefore, it was confirmed that the growth of cancer cell colonies was suppressed depending on the concentration of the mixed extract of the present invention.

Example 6: Identification of Mechanism of Suppressing Cancer Cells by Western Blotting Because the ability of the mixed extract of *Angelica gigas:Aconitum carmichaeli* Debeaux:*Zingiber officinale* Roscoe having a mixing ratio of 2:1:1 according to the present invention to suppress cancer cell growth and colony formation was confirmed in Example 5, an anticancer mechanism of the mixed extract was confirmed in various cancer cells by Western blotting.

Specifically, washed cells were cultured and lysed on ice for 20 minutes using a lysis buffer (50 mM Tris-HCl, pH 7.4, 1% NP-40, 0.25% sodium deoxycholate, 0.1% sodium dodecyl sulfate, 150 mM NaCl, 1 mM ethylenediaminetetraacetic acid, and protease inhibitor), followed by centrifugation at 13,000 rpm at 4° C. Then, the cells were quantified by Bio-Rad Bradford protein assay (Hercules, CA, United States). A total protein was isolated using 6% to 15% sodium dodecyl sulfate (SDS)-polyacrylamide gel and transferred to a Protran nitrocellulose membrane (Whatman, UK), and then the membrane was blocked using 1% BSA supplemented with 1% skim milk and PBS-T (0.1% Tween-20) and treated with a primary antibody. Subsequently, the resultant was treated with an HRP-bound secondary IgG antibody (Calbiochem, San Diego, CA, USA) and evaluated using an enhanced chemiluminescence detection system (Amersham ECL kit, Amersham Pharmacia Biotech Inc., Piscataway, NJ, USA), and the results were identified.

1) Liver Cancer Cell

HEPG2 and SKHEP1 cells, which are liver cancer cells, were treated with the mixed extract of *Angelica gigas:Aconitum carmichaeli* Debeaux:*Zingiber officinale* Roscoe (2:1:1) of the present invention, and the results were identified by the Western blot method.

Figure 1:
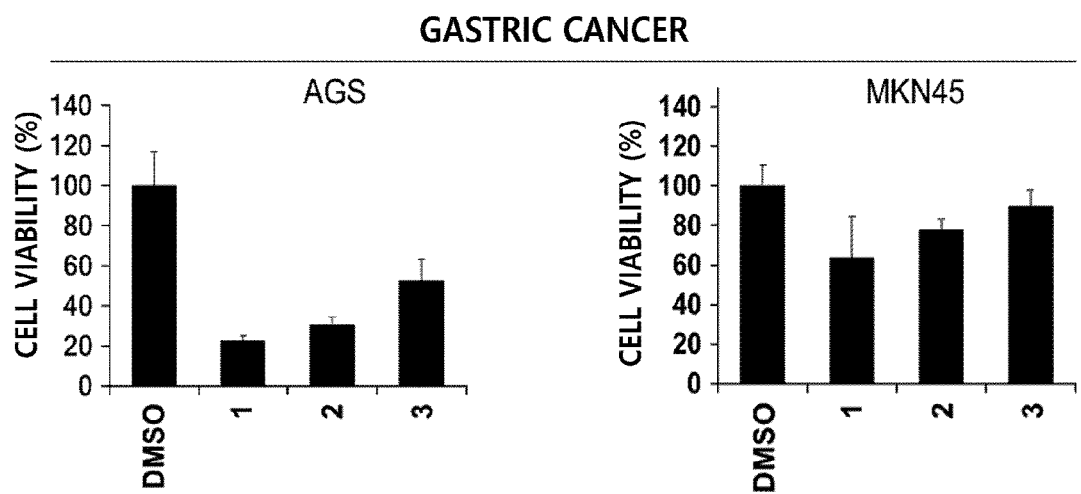
FIG. 1 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of gastric cancer cells measured by an MTT assay.
Figure 2:
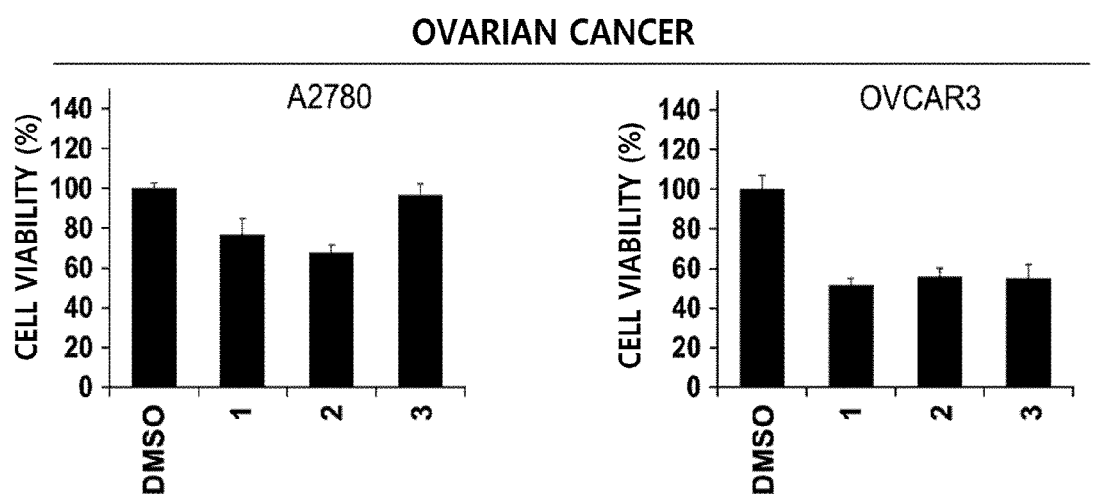
FIG. 2 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of ovarian cancer cells measured by an MTT assay.
Figure 3:
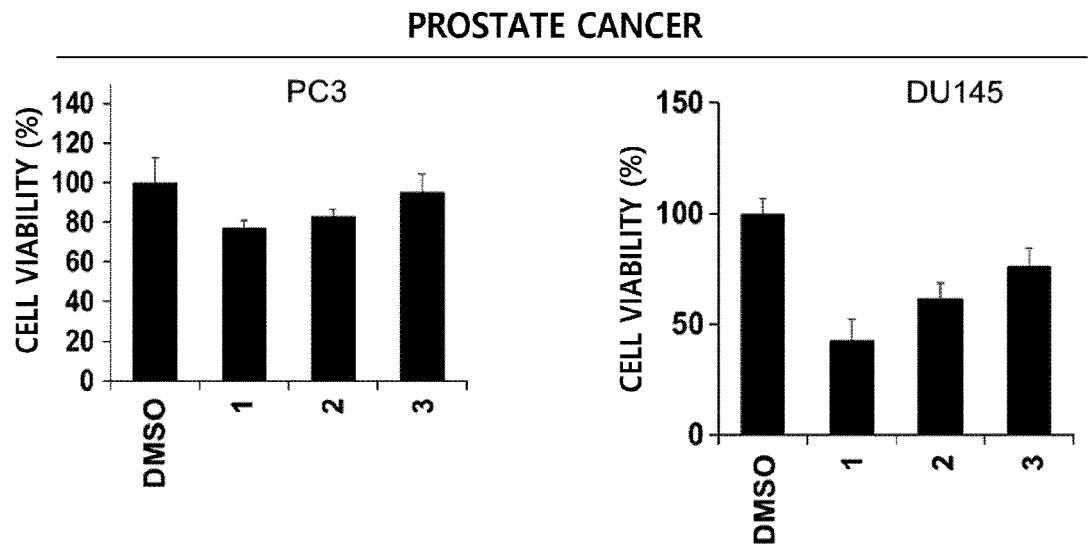
FIG. 3 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of prostate cancer cells measured by an MTT assay.
Figure 4:
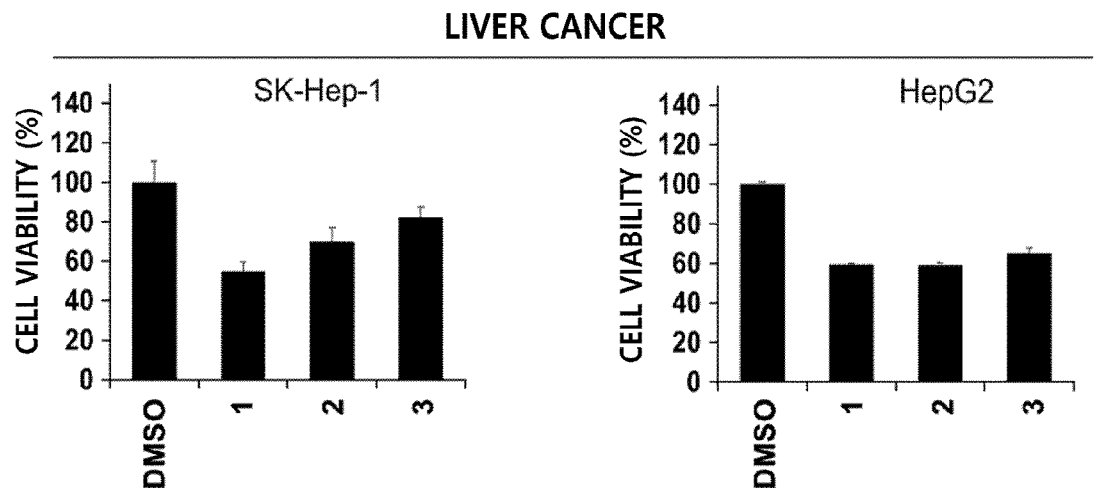
FIG. 4 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of liver cancer cells measured by an MTT assay.
Figure 5:
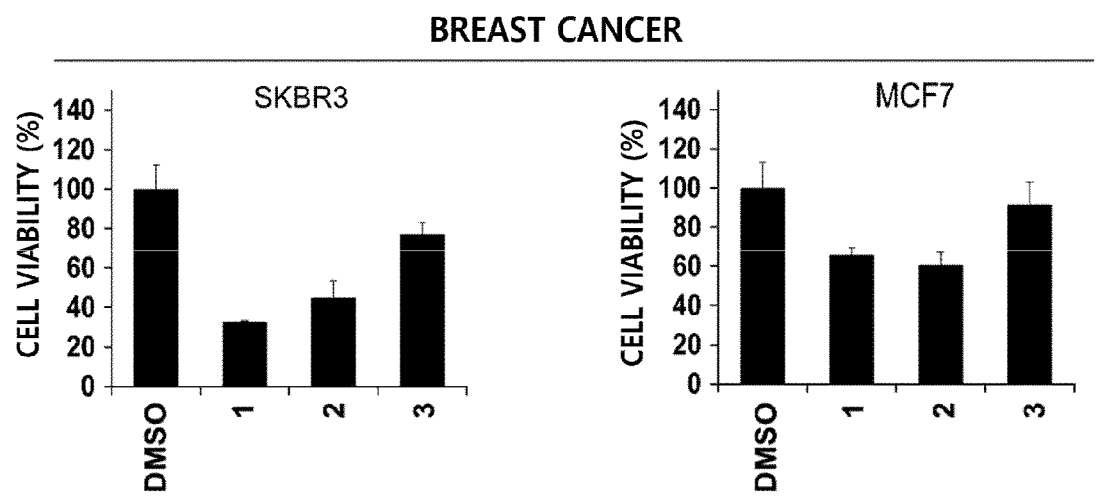
FIG. 5 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of breast cancer cells measured by an MTT assay.
Figure 6:
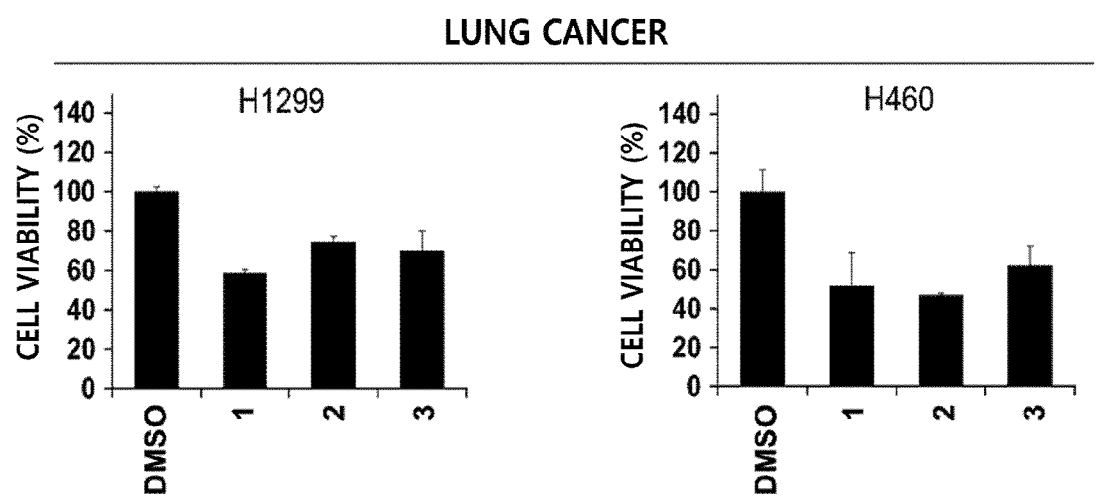
FIG. 6 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of lung cancer cells measured by an MTT assay.
Figure 7:
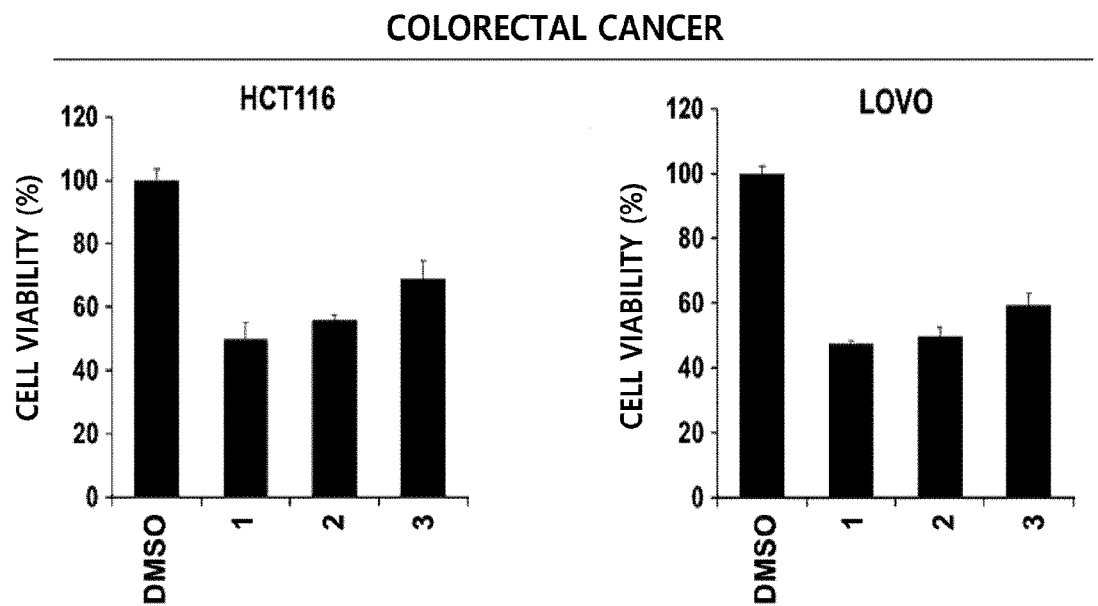
FIG. 7 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on proliferation of colorectal cancer cells measured by an MTT assay.
Figure 8:
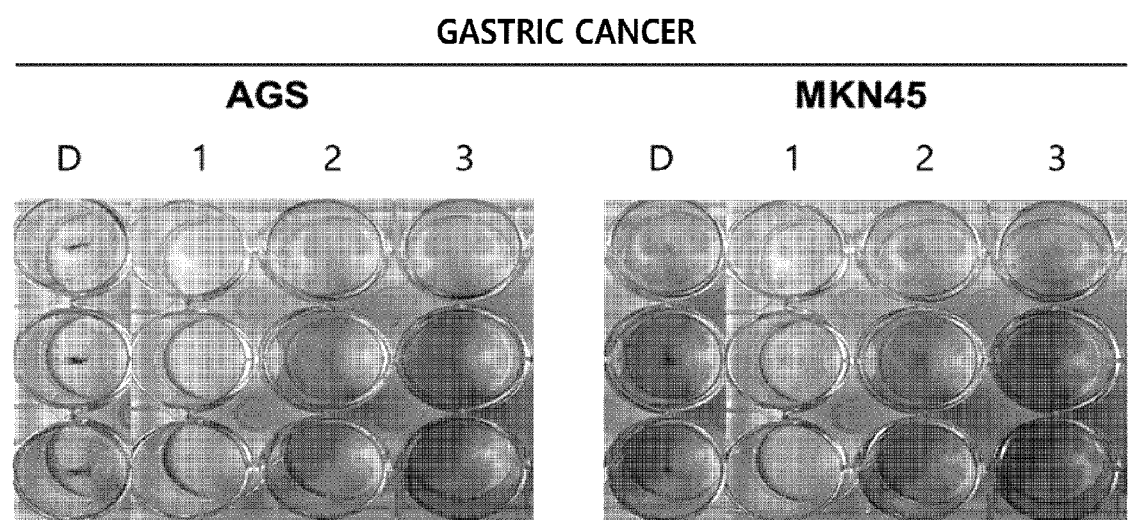
FIG. 8 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of gastric cancer cells measured by a colony formation assay.
Figure 9:
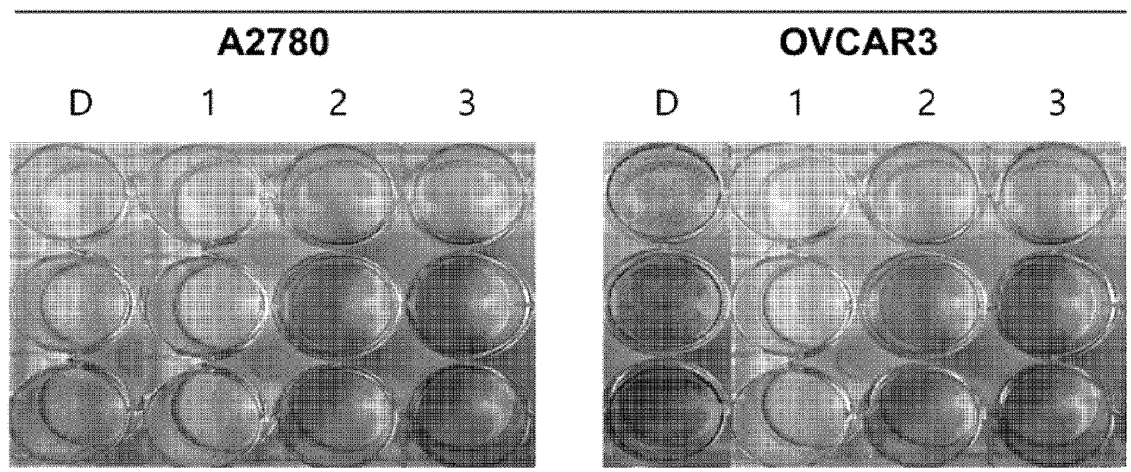
FIG. 9 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of ovarian cancer cells measured by a colony formation assay.
Figure 10:
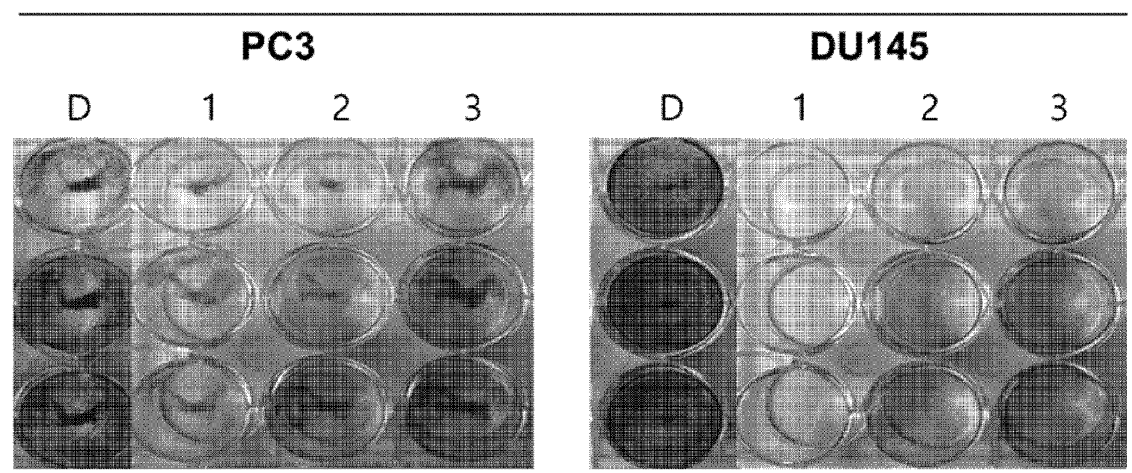
FIG. 10 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of prostate cancer cells measured by a colony formation assay.
Figure 11:
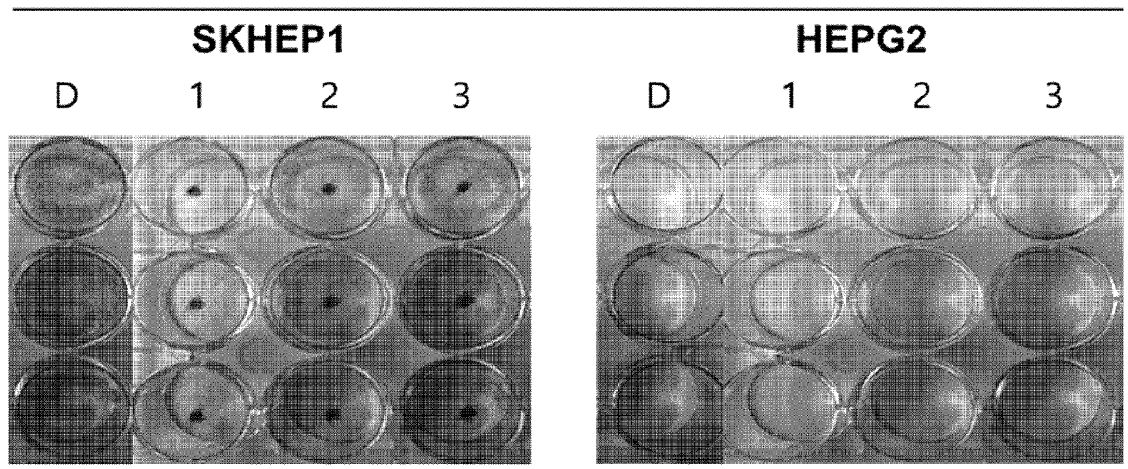
FIG. 11 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of liver cancer cells measured by a colony formation assay.
Figure 12:
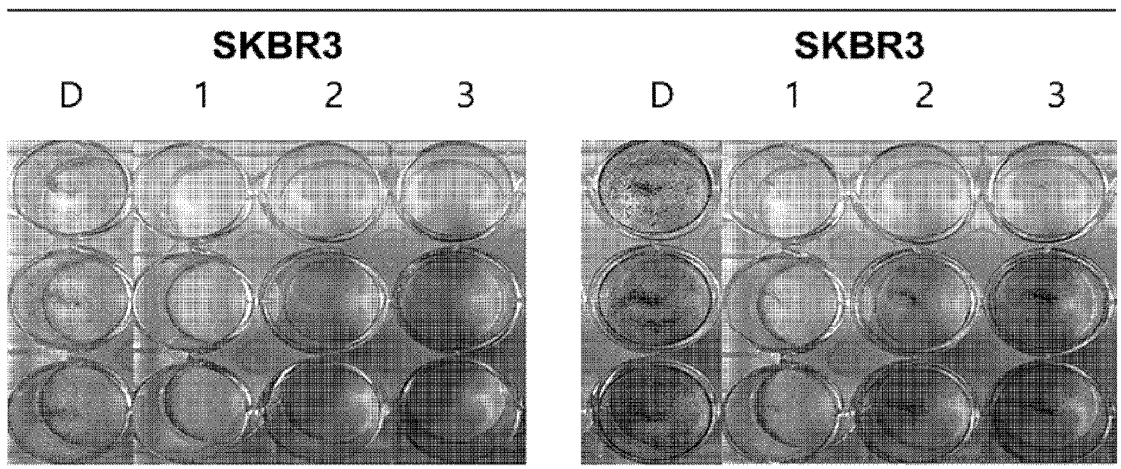
FIG. 12 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of breast cancer cells measured by a colony formation assay.
Figure 13:
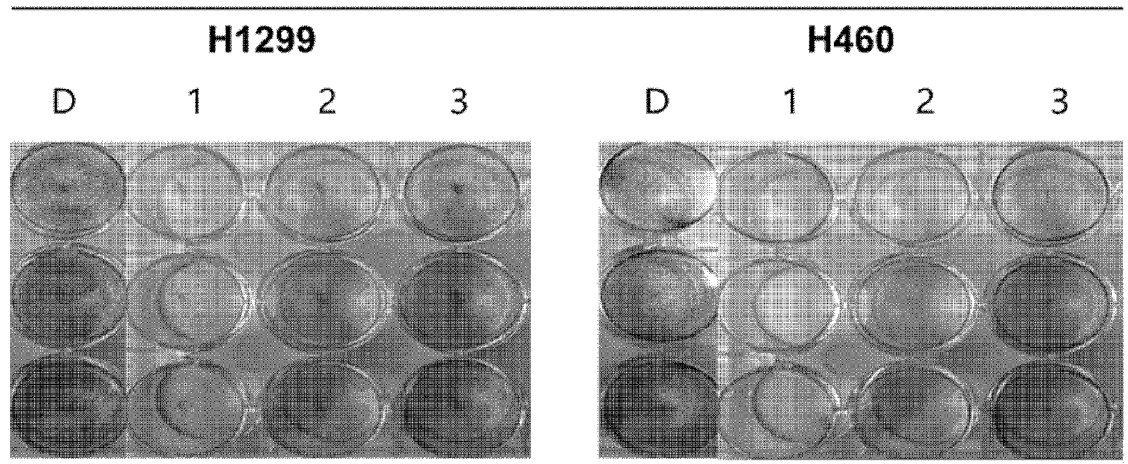
FIG. 13 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of lung cancer cells measured by a colony formation assay.
Figure 14:
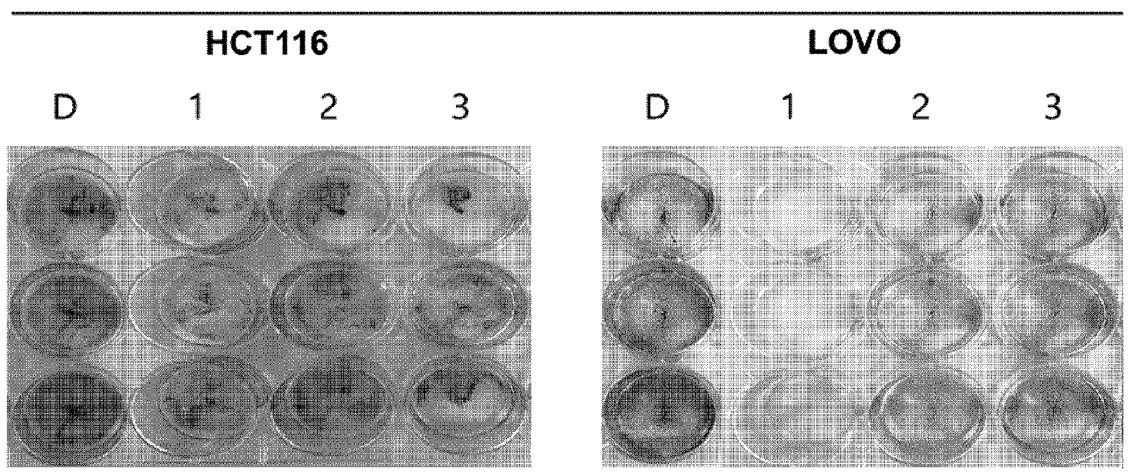
FIG. 14 shows effects of mixed extracts of *Angelica gigas*, *Aconitum carmichaeli* Debeaux, and *Zingiber officinale* Roscoe with various mixing ratios ((1) 2:1:1, (2) 4:1:1, and (3) 2:3:1) on colony formation of colorectal cancer cells measured by a colony formation assay.
Figure 15:
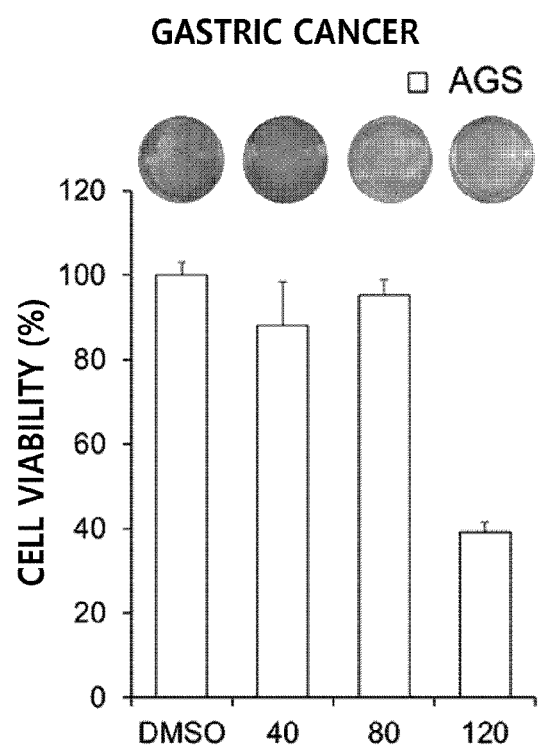
FIG. 15 shows effects of a mixed extract of *Angelica gigas*, *Aconitum carmichaeli* Debeaux, and *Zingiber officinale* Roscoe with a mixing ratio of 2:1:1 on colony formation and cell viability of gastric cancer cells measured by an MTT assay and a colony formation assay.
Figure 16:
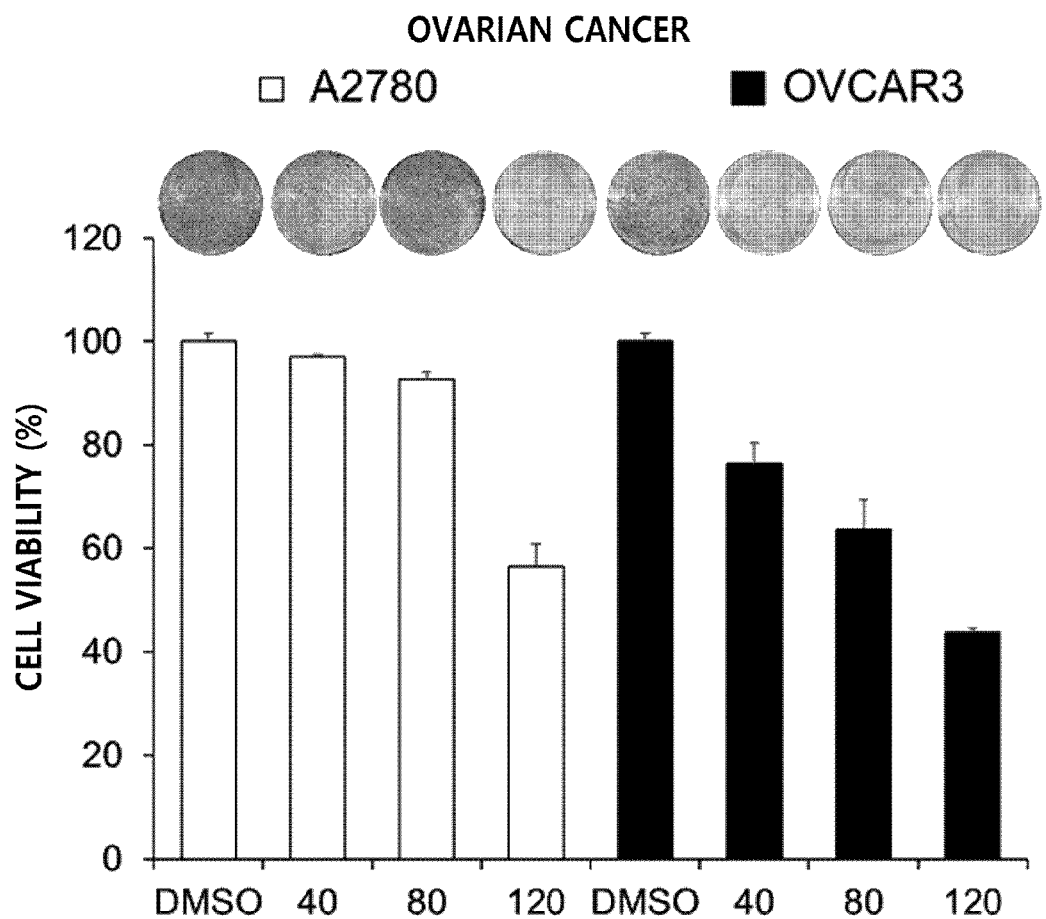
FIG. 16 shows effects of a mixed extract of *Angelica gigas*, *Aconitum carmichaeli* Debeaux, and *Zingiber officinale* Roscoe with a mixing ratio of 2:1:1 on colony formation and cell viability of ovarian cancer cells measured by an MTT assay and a colony formation assay.
Figure 17:
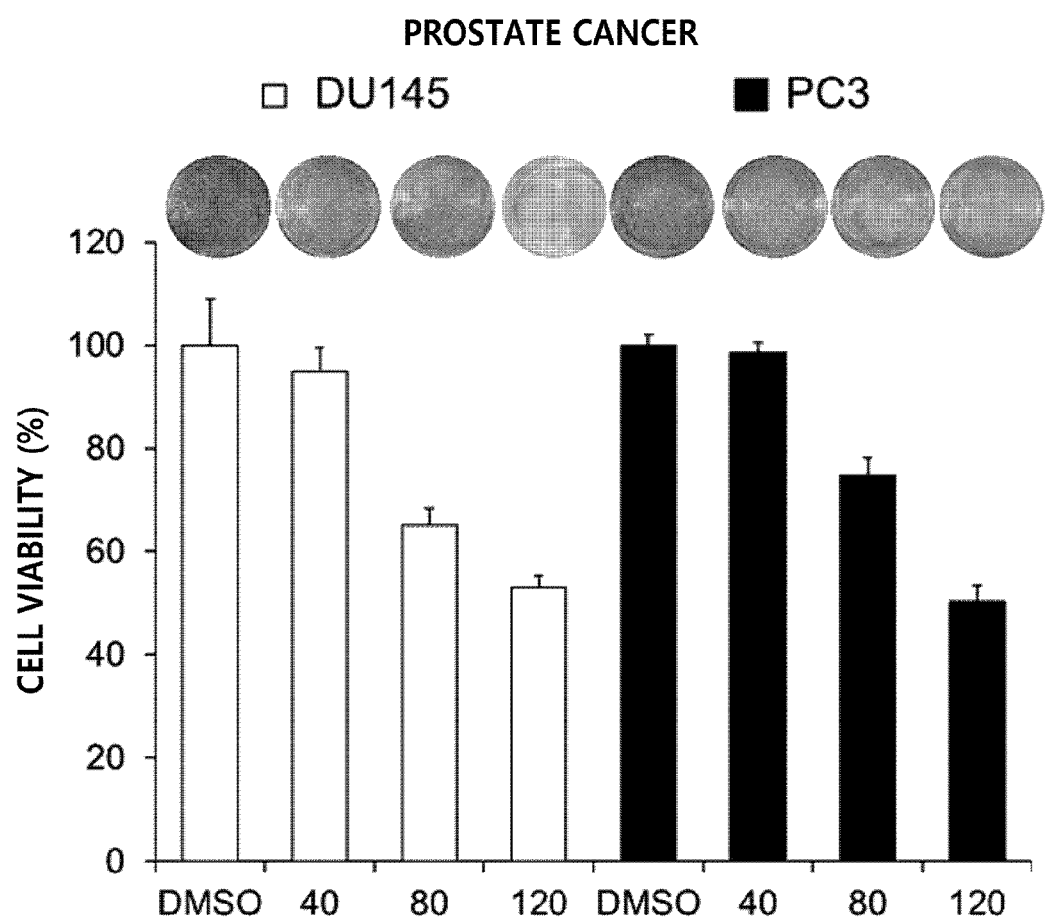
FIG. 17 shows effects of a mixed extract of *Angelica gigas*, *Aconitum carmichaeli* Debeaux, and *Zingiber officinale* Roscoe with a mixing ratio of 2:1:1 on colony formation and cell viability of prostate cancer cells measured by an MTT assay and a colony formation assay.
Figure 18:
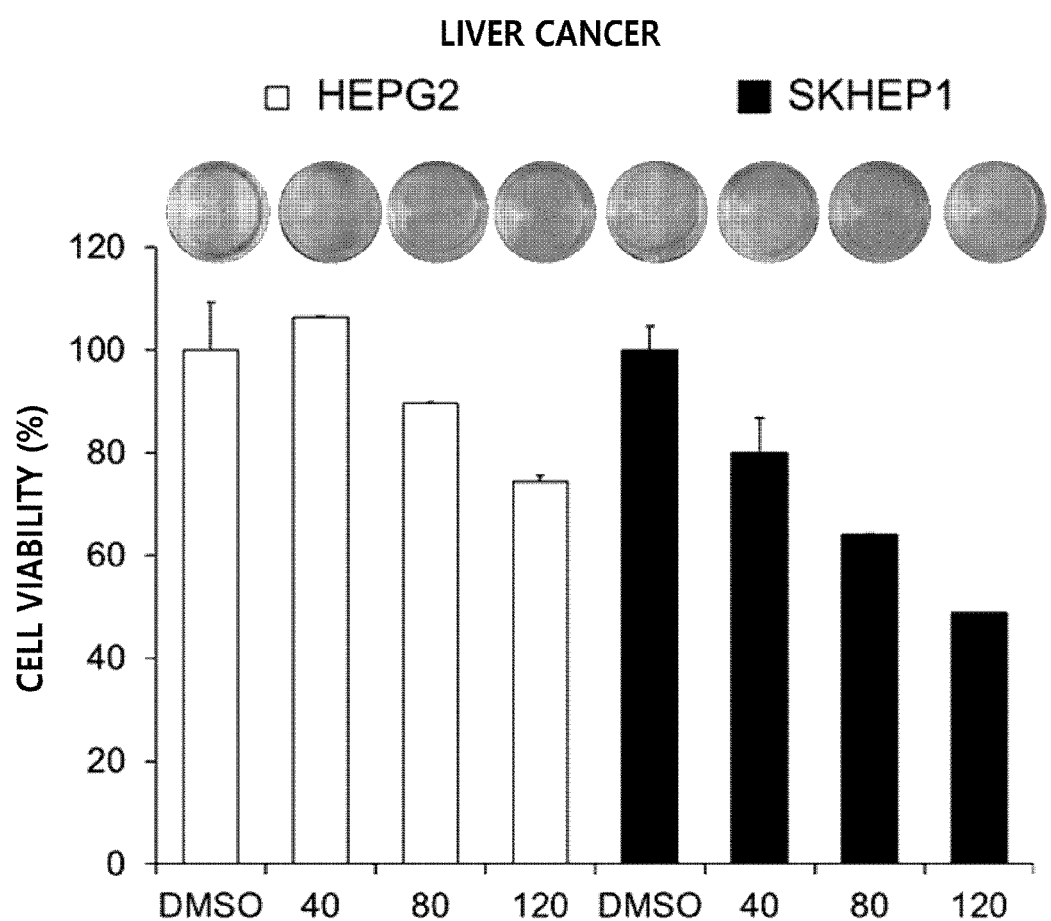
FIG. 18 shows effects of a mixed extract of *Angelica gigas*, *Aconitum carmichaeli* Debeaux, and *Zingiber officinale* Roscoe with a mixing ratio of 2:1:1 on colony formation and cell viability of liver cancer cells measured by an MTT assay and a colony formation assay.
Figure 19:
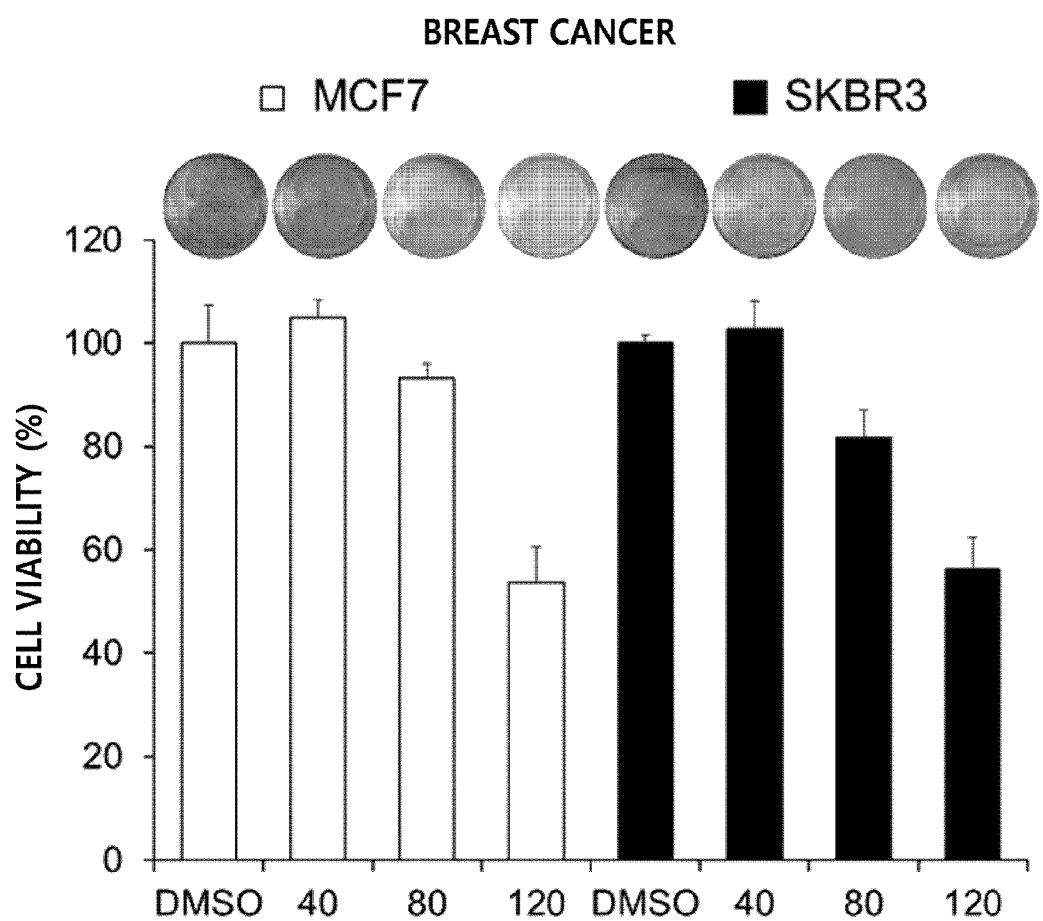
FIG. 19 shows effects of a mixed extract of *Angelica gigas*, *Aconitum carmichaeli* Debeaux, and *Zingiber officinale* Roscoe with a mixing ratio of 2:1:1 on colony formation and cell viability of breast cancer cells measured by an MTT assay and a colony formation assay.
Figure 20:
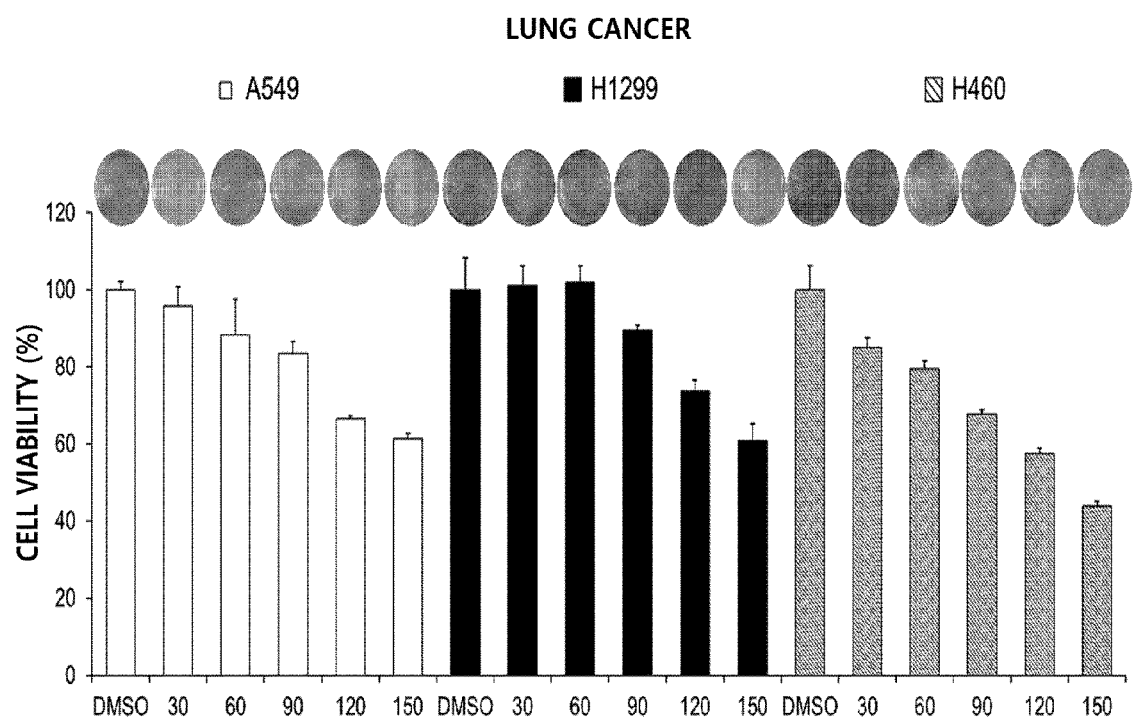
FIG. 20 shows effects of a mixed extract of *Angelica gigas*, *Aconitum carmichaeli* Debeaux, and *Zingiber officinale* Roscoe with a mixing ratio of 2:1:1 on colony formation and cell viability of lung cancer cells measured by an MTT assay and a colony formation assay.
Figure 21:
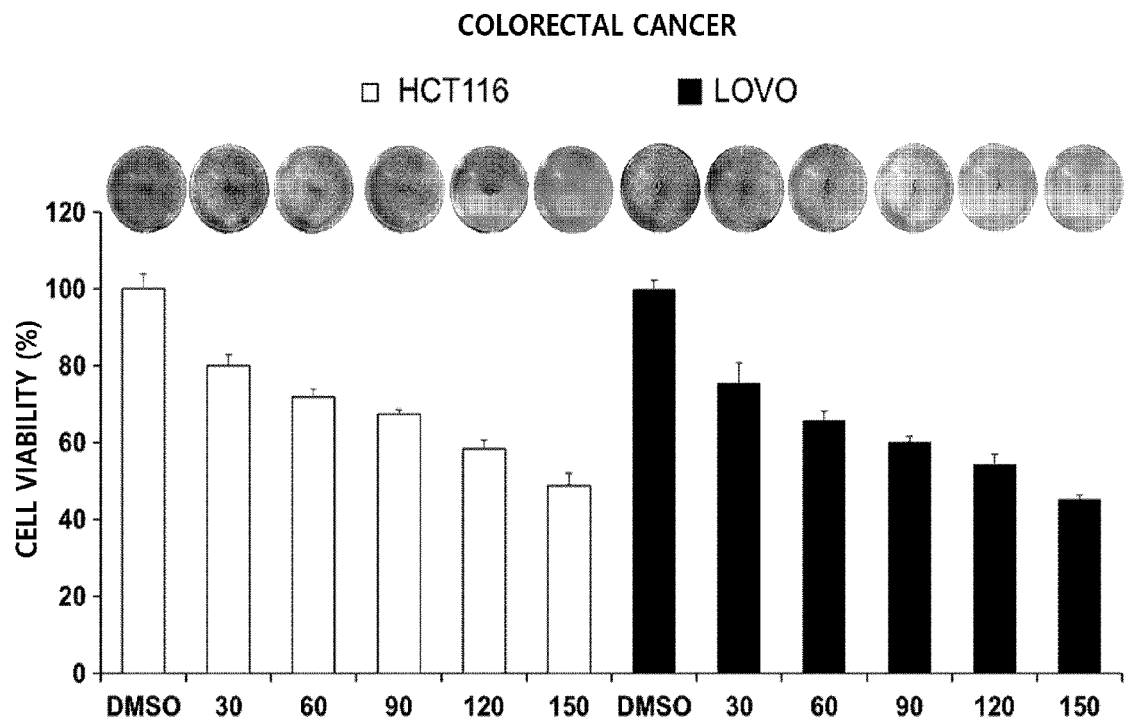
FIG. 21 shows effects of a mixed extract of *Angelica gigas*, *Aconitum carmichaeli* Debeaux, and *Zingiber officinale* Roscoe with a mixing ratio of 2:1:1 on colony formation and cell viability of colorectal cancer cells measured by an MTT assay and a colony formation assay.
Figure 22:
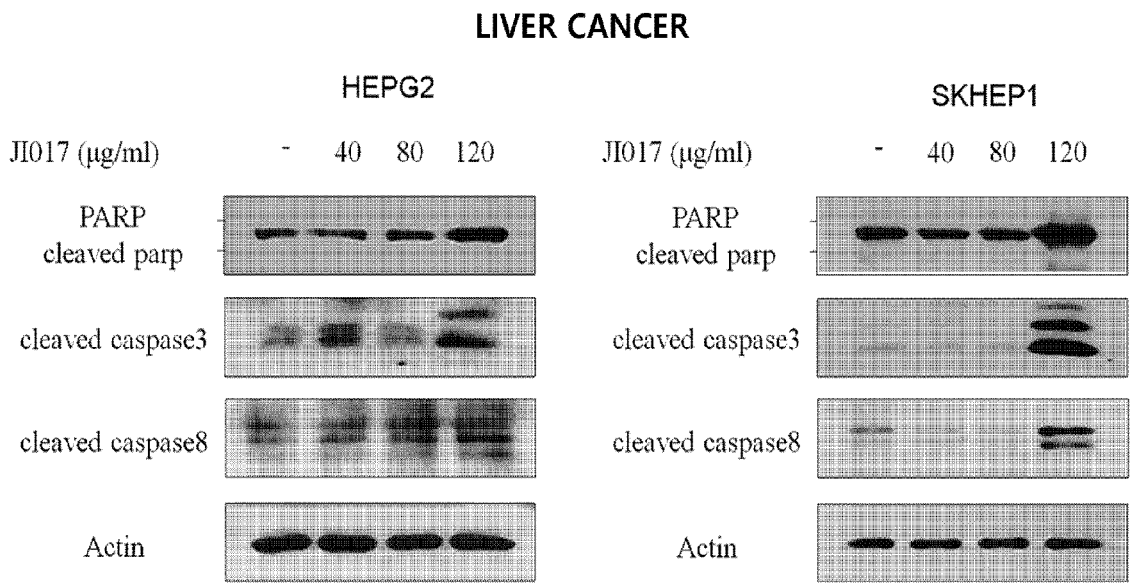
FIG. 22 is photographs showing an anticancer mechanism of a mixed extract of *Angelica gigas*, *Aconitum carmichaeli* Debeaux, and *Zingiber officinale* Roscoe with a mixing ratio of 2:1:1 in liver cancer cells evaluated by Western blot analysis.

As a result, as shown in FIG. 22, induction of apoptosis was confirmed via reaction with caspase 3, caspase 9, and PARP.

2) Lung Cancer Cell

A549, H460, and H1299 cells, which are lung cancer cells, were treated with the mixed extract of *Angelica gigas:Aconitum carmichaeli* Debeaux:*Zingiber officinale* Roscoe (2:1:1) of the present invention, and the results were identified by the Western blot method.

Figure 23:
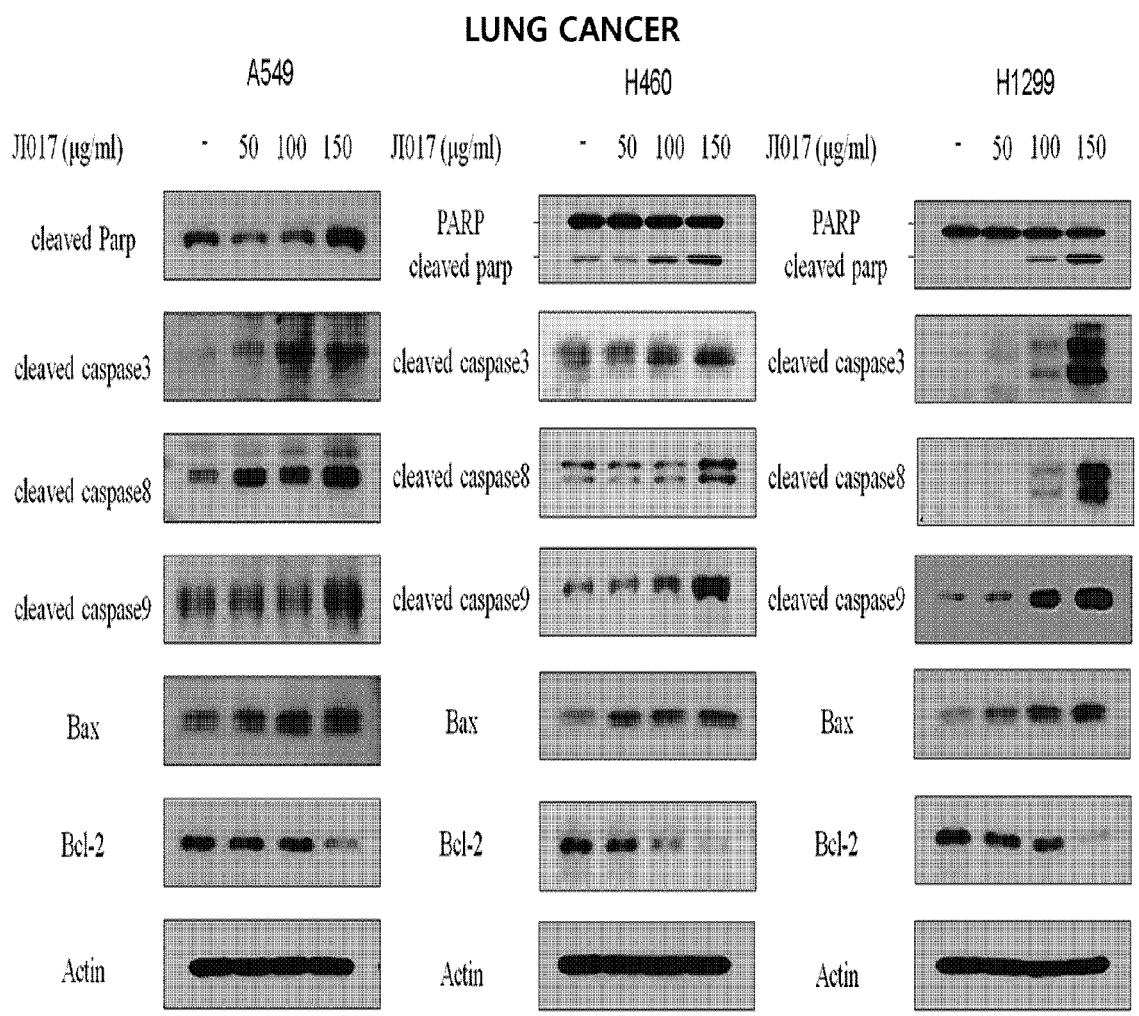
FIG. 23 is photographs showing an anticancer mechanism of a mixed extract of *Angelica gigas*, *Aconitum carmichaeli* Debeaux, and *Zingiber officinale* Roscoe with a mixing ratio of 2:1:1 in lung cancer cells evaluated by Western blot analysis.

As a result, as shown in FIG. 23, induction of apoptosis was confirmed via reaction with caspase 3, caspase 9, and PARP.

3) Prostate Cancer Cell

DU145 and PC3 cells, which are liver cancer cells, were treated with the mixed extract of *Angelica gigas:Aconitum carmichaeli* Debeaux:*Zingiber officinale* Roscoe (2:1:1) of the present invention, and the results were identified by the Western blot method.

Figure 24:
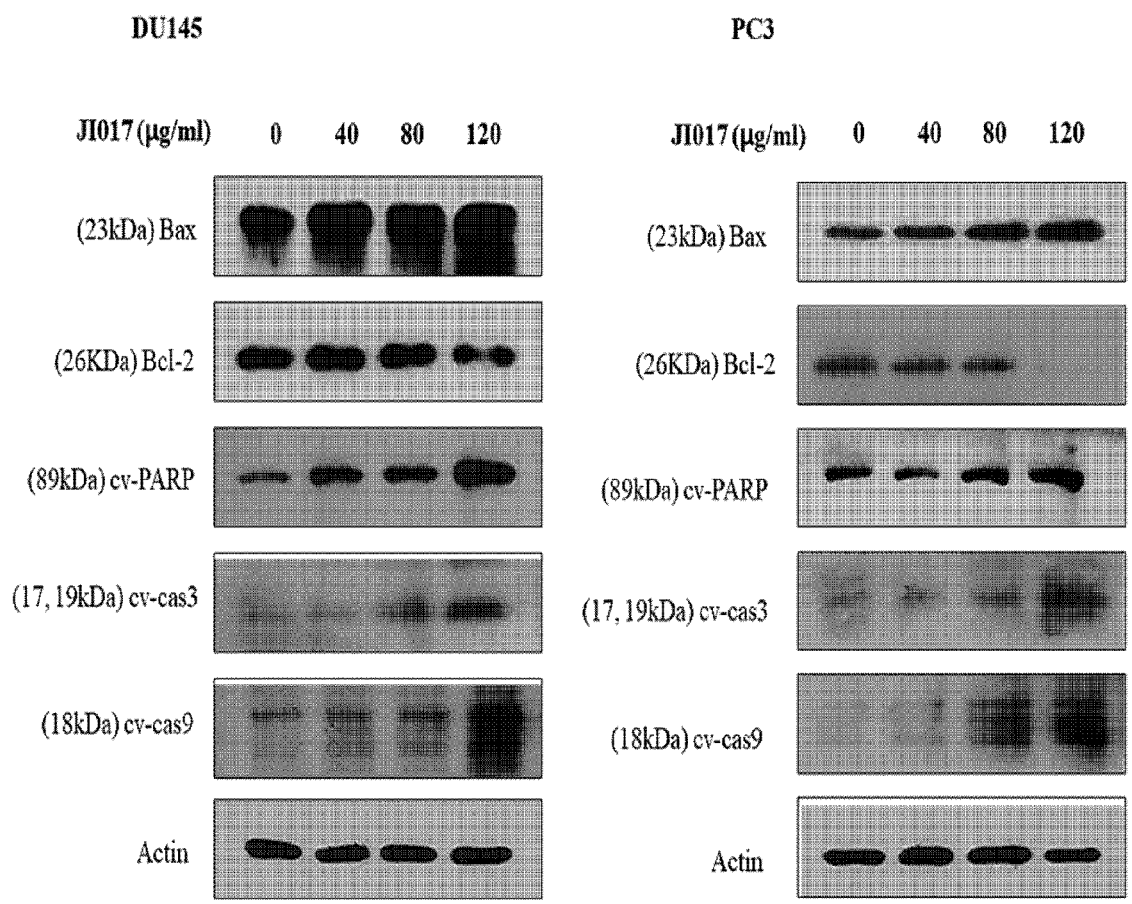
FIG. 24 is photographs showing an anticancer mechanism of a mixed extract of *Angelica gigas*, *Aconitum carmichaeli* Debeaux, and *Zingiber officinale* Roscoe with a mixing ratio of 2:1:1 in prostate cancer cells evaluated by Western blot analysis.

As a result, as shown in FIG. 24, induction of apoptosis was confirmed via reaction with caspase 3, caspase 9, and PARP.

4) Gastric Cancer Cell

AGS cells, which are gastric cancer cells, were treated with the mixed extract of *Angelica gigas:Aconitum carmichaeli* Debeaux:*Zingiber officinale* Roscoe (2:1:1) of the present invention, and the results were identified by the Western blot method.

Figure 25:
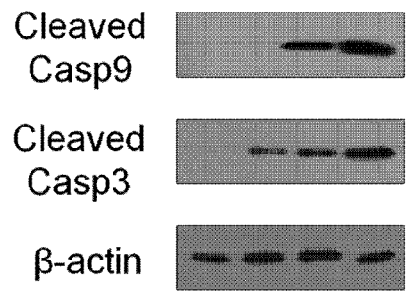
FIG. 25 is photographs showing an anticancer mechanism of a mixed extract of *Angelica gigas*, *Aconitum carmichaeli* Debeaux, and *Zingiber officinale* Roscoe with a mixing ratio of 2:1:1 in gastric cancer cells evaluated by Western blot analysis.

As a result, as shown in FIG. 25, induction of apoptosis was confirmed via reaction with caspase 3, caspase 9, and PARP.

5) Ovarian Cancer Cell

A2780 cells, which are ovarian cancer cells, were treated with the mixed extract of *Angelica gigas:Aconitum carmichaeli* Debeaux:*Zingiber officinale* Roscoe (2:1:1) of the present invention, and the results were identified by the Western blot method.

Figure 26:
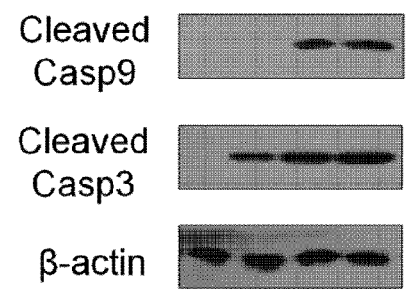
FIG. 26 is photographs showing an anticancer mechanism of a mixed extract of *Angelica gigas*, *Aconitum carmichaeli* Debeaux, and *Zingiber officinale* Roscoe with a mixing ratio of 2:1:1 in ovarian cancer cells evaluated by Western blot analysis.

As a result, as shown in FIG. 26, induction of apoptosis was confirmed via reaction with caspase 3, caspase 9, and PARP.

6) Colorectal Cancer Cell

HCT-116 cells, which are colorectal cancer cells, were treated with the mixed extract of *Angelica gigas:Aconitum carmichaeli* Debeaux:*Zingiber officinale* Roscoe (2:1:1) of the present invention, and the results were identified by the Western blot method.

Figure 27:
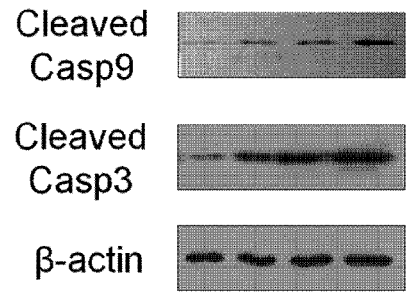
FIG. 27 is photographs showing an anticancer mechanism of a mixed extract of *Angelica gigas*, *Aconitum carmichaeli*

As a result, as shown in FIG. 27, induction of apoptosis was confirmed via reaction with caspase 3, caspase 9, and PARP.

7) Breast Cancer Cell

MCF-7 cells, which are breast cancer cells, were treated with the mixed extract of *Angelica gigas:Aconitum carmichaeli* Debeaux:*Zingiber officinale* Roscoe (2:1:1) of the present invention, and the results were identified by the Western blot method.

As a result, as shown in FIG. 28, induction of apoptosis was confirmed via reaction with caspase 3, caspase 9, and PARP.

Based thereon, it was confirmed that the mixed extract of *Angelica gigas:Aconitum carmichaeli* Debeaux:*Zingiber officinale* Roscoe with a mixing ratio of 2:1:1 according to the present invention induces apoptosis in various cancer cells, and thus anticancer effects thereof were confirmed.

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the disclosure.

The invention claimed is:

1. A method for treating cancer, the method comprising administering a pharmaceutical composition comprising a mixed extract of *Angelica gigas*, *Aconitum carmichaeli* Debeaux, and *Zingiber officinale* Roscoe as an active ingredient, wherein the extract is an ethanol extract, and wherein a mixing ratio of the extract of *Angelica gigas*, *Aconitum carmichaeli* Debeaux, and *Zingiber officinale* Roscoe is 1.5 to 2.5:0.5 to 1.5:0.5 to 1.5.

2. The method according to claim 1, wherein a content of the extract is from 0.0001 wt % to 20 wt % based on a total weight of the composition.

3. The method according to claim 1, further comprising a pharmaceutically acceptable carrier, an excipient, or a diluent.

4. The method according to claim 1, wherein the cancer is gastric cancer, ovarian cancer, prostate cancer, liver cancer, breast cancer, lung cancer, or colorectal cancer.

* * * * *